United States Patent [19]

Kapitanov

[11] 4,204,541

[45] May 27, 1980

[54] SURGICAL INSTRUMENT FOR STITCHING UP SOFT TISSUES WITH LENGTHS OF SPIKED SUTURE MATERIAL

[76] Inventor: Nikolai N. Kapitanov, ulitsa Levchenko, 3, kv. 9, Moscow, U.S.S.R.

[21] Appl. No.: 866,564

[22] Filed: Jan. 3, 1978

[30] Foreign Application Priority Data

Jan. 24, 1977 [SU] U.S.S.R. ............... 2447214

[51] Int. Cl.² ........................................... A61B 17/04
[52] U.S. Cl. ..................... 128/334 R; 128/335.5; 128/339; 128/340
[58] Field of Search ............. 128/334, 336, 337, 339, 128/340, 335.5, 217, 334 R

[56] References Cited

U.S. PATENT DOCUMENTS

| | | | |
|---|---|---|---|
| 3,123,077 | 3/1964 | Alcamo | 128/335.5 |
| 3,716,058 | 2/1973 | Tanner | 128/337 |
| 3,820,545 | 6/1974 | Jefferts | 128/217 X R |

FOREIGN PATENT DOCUMENTS

| | | | |
|---|---|---|---|
| 295962 | 12/1916 | Fed. Rep. of Germany | 128/339 |
| 6714 | of 1897 | United Kingdom | 128/334 R |
| 1358466 | 7/1974 | United Kingdom | 128/334 R |

Primary Examiner—Edgar S. Burr
Assistant Examiner—James R. Feyrer
Attorney, Agent, or Firm—Steinberg and Blake

[57] ABSTRACT

A surgical instrument for stitching up soft tissues with lengths of spiked suture material comprises a hollow body which houses a tubular needle having a through bore adapted to accommodate said length of suture material to be introduced into the tissue being sutured along with the needle, and a stop stationary with respect to the body and accommodated inside the through bore of the needle. Both the needle and the stop are shaped as coils having the same diameter and lead, and the needle is mounted slidably along the stop so as to retain the length of suture material in the tissue being sutured while extracting the needle therefrom.

2 Claims, 9 Drawing Figures

SURGICAL INSTRUMENT FOR STITCHING UP SOFT TISSUES WITH LENGTHS OF SPIKED SUTURE MATERIAL

BACKGROUND OF THE INVENTION

The present invention relates to medical equipment and has particular reference to surgical instruments for stitching up soft tissues; the instrument may be applied predominantly for suturing thick-walled organs, e.g., the walls of the left ventricle of the heart or of the liver, with lengths of spiked suture material which may be a metal or a dissolvable matter.

A surgical instrument for stitching up soft tissues with lengths of spiked suture material is known (cf. an earlier filed application by the same inventor, having a Convention priority date of Mar. 11, 1977), said instrument comprising a hollow body which houses a tubular needle having a through bore adapted to accommodate a length of spiked suture material to be introduced into the tissue being sutured along with the needle, and a stop stationary with respect to the body and accommodated inside the through bore of the needle. The needle is mounted slidably along the stop so as to retain the length of suture material in the tissue being stitched while extracting the needle therefrom. In addition, the needle has a drive to move along the stop, said drive being defined by a cylindrical rod running inside the body so as to envelope the stem carrying the stop, said rod terminating at one of its ends in a handgrip, while the other end thereof has a tapered hole adapted to engage a tapered sleeve serving for a detachable mounting of the needle at the rod end.

The afore-discussed surgical instrument for stitching up soft tissues with lengths of spiked suture material operates as follows.

The tapered sleeve of the tubular needle with a length of suture material is fitted into the tapered hole of the cylindrical rod of the instrument to make the latter ready for operation. Then, the needle is pricked at the juxtaposed lips of the wound in a soft tissue in such a manner that the needle should pass through both of the wound lips. Next, with the body of the instrument not withdrawn from the surface of the tissue being sutured, one must retract the handgrip of the instrument upwards, thus causing the needle to slide along the stop to be extracted from the tissue, whereas the stop and the length of suture material thrusting thereagainst remain immobile, and the length of suture material is left in the tissue, thus holding together the wound margins. This done, the instrument is withdrawn from the thus-established suture. To apply a next suture, the used-up needle is replaced by the one charged with suture material.

The afore-described known instrument is capable of suturing soft tissues of any thickness throughout the depth of incision, which adds to the regeneration rate of the tissues lying in the plane of incision in deeply seated wounds due to an improved contact of the dissected tissues being sutured. However, the instrument proves to be inapplicable in cases where some vital blood vessels, ducts, or nerves run nearby the wound margin (e.g., when the margin of the wound on the heart lied close to the coronary artery) this being accounted for by the fact that said instrument is applicable for suturing deeply seated wounds only when rather long distances from the wound margin to the point of the needle introduction into the tissue are available, since the needle should make up an angle with the wound incision, the thicker the tissue being sutured the longer the above distance.

SUMMARY OF THE INVENTION

It is a primary object of the present invention to provide a surgical instrument for stitching up soft tissues with lengths of spiked suture material that will ensure suture application in close vicinity to the line incision.

The invention resides in that in a surgical instrument for stitching up soft tissues with lengths of spiked suture material, comprising a hollow body which houses a tubular needle having a through bore adapted to accommodate said length of suture material to be introduced into the tissue being sutured along with the needle, and a stop stationary with respect to the body and accommodated inside the through bore of the needle, said needle being mounted slidably along the stop so as to retain the length of suture material in the tissue being sutured while extracting the needle therefrom, according to the invention, both the needle and the stop are shaped as coils having the same mean diameter and lead.

Such an embodiment of the instrument provides for quick and reliable suturing of the tissue of deep-seated wounds over the entire place of incision by applying sutures with lengths of spiked suture material, involving a minimum area of the organ being sutured into the suture formation zone due to applying a suture immediately to the line of incision, which adds to the regeneration rate of the tissue involved in the surgery owing to eliminating any possibility of forming an inner nook and makes for healing the wound by first intention.

Furthermore, the proposed construction of the instrument enables one to suture using a dissolvable material, such as biopolymers.

The instrument is applicable both for stitching together the walls of internal and parenchymatous organs and the margins of superficial wounds.

The instrument is capable of higher manoeuvrability when applying sutures.

It is expedient that the needle be provided with a screw drive to impart thereto motion along the stop.

The above feature provides for a smooth, jerkless and uniform motion of the tubular needle along the stop, while being extracted from the tissue being sutured, which adds to the quality of the suture applied.

DESCRIPTION OF THE DRAWINGS

In what follows, the present invention is illustrated in a disclosure of preferred embodiments thereof with reference to the accompanying drawings, wherein.

DESCRIPTION OF THE PREFERRED EMBODIMENTS

Figure 4:
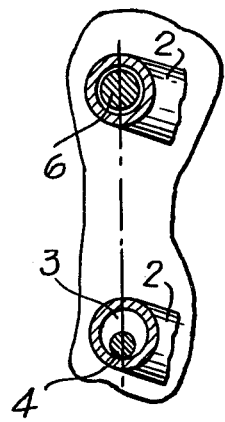
FIG. 4 is a scaled-up view of portion IV of the tubular needle of FIG. 1.
Figure 3:
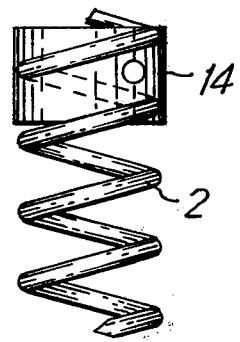
FIG. 3 is an enlarged-scale view of a tubular needle with a cylindrical sleeve, according to the invention.
Figure 5:
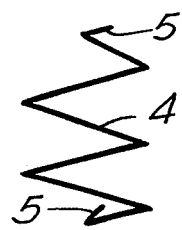
FIG. 5 is a length of spiked suture material used in the instrument according to the invention.
Figure 6:
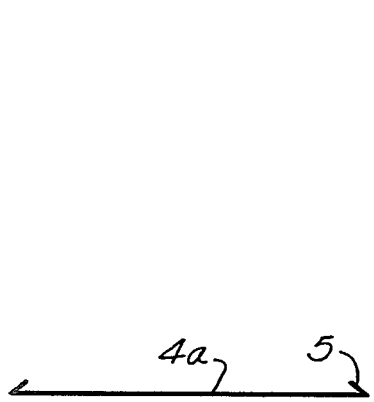
FIG. 6 is another embodiment of a length of suture material used in the instrument according to the invention.

Referring now to the accompanying drawings, the surgical instrument for stitching up soft tissues with lengths of spiked suture material comprises a hollow body 1 (FIGS. 1, 2) which houses a tubular needle 2 (FIGS. 1,2,3) having a through bore 3 (FIG. 4) adapted for accommodating a length 4 of suture material provided with spikes 5 (FIG. 5). The length 4 of suture material is coil-shaped, though it may also be shaped as a flexible rod, like a length 4a (FIG. 6), whereas used as the suture material may be a metal (shaped as a wire), or a dissolvable material such as biopolymers. The through bore 3 (FIG. 4) of the needle 2 accommodates a stop 6 (FIGS. 1,2,4) adapted for needle 2 to slide therealong and for retaining the length 4 of suture material in the tissue being sutured. Both the tubular needle 2 and the stop 6 are shaped as coils having the same mean diameter and lead so as to enable the needle 2 to slide along the stop 6.

The body 1 (FIGS. 1,2) is held positively to a hollow cylinder 8 through a screw 7, the stop 6 being attached to the cylinder 8 by means of a ring 9.

Figure 1:
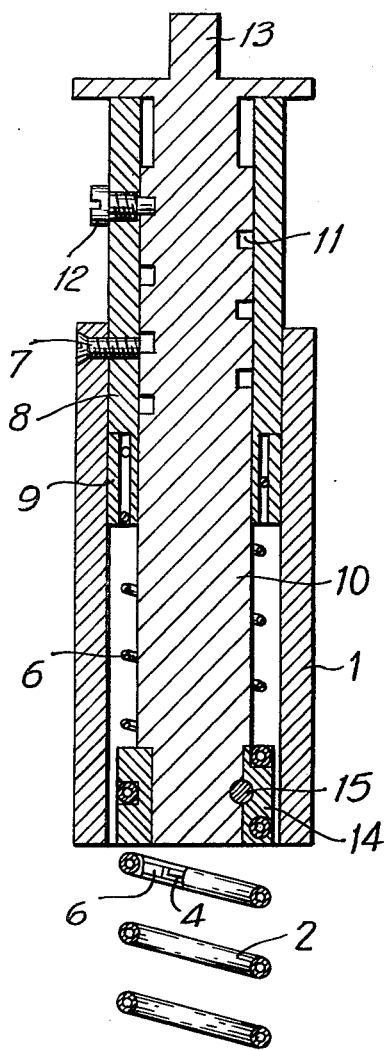
FIG. 1 is a longitudinal-section view of a surgical instrument for stitching up soft tissues with lengths of spiked suture material, according to the invention.
Figure 2:
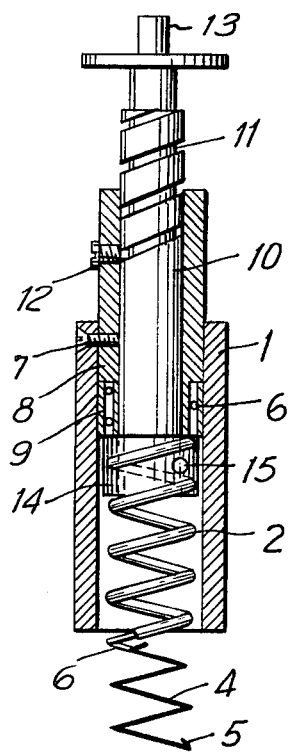
FIG. 2 is a fragmentary cutaway view of the instrument of FIG. 1 as shown in the position where the tubular needle is screwed all the way onto the stop, and the suture material is brought out from the needle.

The needle 2 has a screw drive to slide along the stop 6, said drive being provided by a cylindrical rod 10 running inside the hollow cylinder 8 and having a screw thread 11 adapted to engage a stud pin 12. The cylindrical rod 10 terminates at one of its ends in a lug 13 to be rotated by, whereas the other end of the rod 10 is shaped as a cylindrical shoulder onto which a cylindrical sleeve 14 (FIGS. 1,2,3) is fitted to provide a detachable mounting of the needle 2 at the end of the rod 10 (FIGS. 1,2). To lock the sleeve 14 on the rod 10, a pin 15 is provided.

The surgical instrument for stitching up soft tissues with lengths of spiked suture material operates as follows.

The instrument as shown in FIG. 1 is ready for operation.

Figure 7:
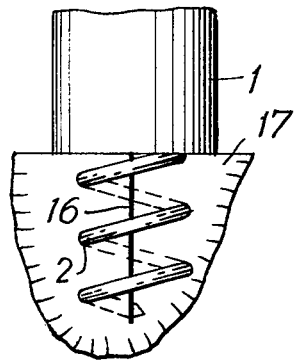
FIG. 7 represents a technique for introducing the instrument needle into the juxtaposed wound lips, according to the invention.
Figure 9:
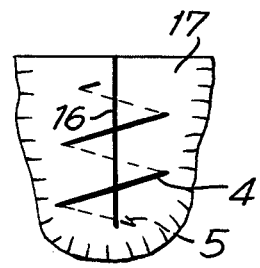
FIG. 9 shows a suture resulting from stitching up soft tissues by the instrument, according to the invention.
Figure 8:
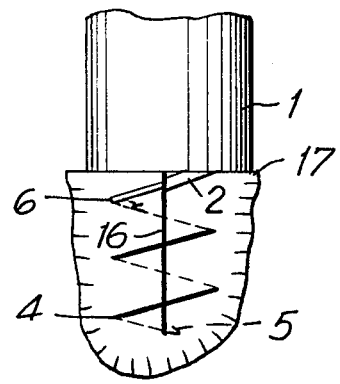
FIG. 8 represents a technique for extracting the instrument needle from the tissue having been stitched up.

The tubular coil-shaped needle 2 is introduced into the justaposed margins of a wound 16 (FIG. 7) by rotating the instrument clockwise till the body 1 contacts the surface of a tissue 17 in such a manner that the needle should prick at both of the lips of the wound 16. Thereupon, with the body 1 not withdrawn from the surface of the tissue 17, one must rotate the rod 10 (FIG. 1) counterclockwise by the lug 13 till the screw 12 thrusts against the end of the screw thread 11 as shown in FIG. 2. As a result, the stop 6 (FIGS. 2, 8) and the length 4 of suture material resting thereagainst remain immobile so that the length 4 of suture material is left in the suture 17 (FIG. 8) to hold together the margins of the wound 16. This done, one must withdraw the instrument from the wound, and the margins of the wound 16 get stitched together as shown in FIG. 9. To place a next suture one must remove the needle 2 (FIG. 3) along with the sleeve 14 from the rod 10 (FIG. 1) and the stop 6 and load the needle with the next length 4 of suture material, whereupon the needle 2 is fitted again into the instrument, and the wound is stitched with the next length 4 of suture material.

What is claimed is:

1. A surgical instrument for suturing soft tissues with lengths of spiked suture material, comprising: a hollow body having an axial bore formed therein; a needle housed within said bore of said body, said needle being movable with respect to said body and having a longitudinal bore formed therethrough adapted to accommodate a length of suture material adapted for introduction along with said needle into the tissue being sutured; a stop fixedly mounted in said bore of said body such that it is stationary with respect thereto, at least a portion of said stop extending within said bore of the needle; said needle and said stop each being shaped as coils having the same mean diameter and lead; said needle being movably mounted in the body such that upon movement of said needle relative to said body to extract the same therefrom, said needle will slide relative to said stop which is fixed with respect to said body whereupon said length of suture material is pushed from within said needle bore by said stop and remain in the tissue being stitched.

2. A surgical instrument as claimed in claim 1, further including screw drive means for imparting to the needle a sliding motion with respect to the stop.

* * * * *